United States Patent [19]

Grimmer et al.

[11] Patent Number: 5,210,023
[45] Date of Patent: May 11, 1993

[54] METHOD OF PURIFYING FERMENT-PRODUCED RIBOFLAVIN

[75] Inventors: Johannes Grimmer, Ludwigshafen; Hans Kiefer, Wachenheim; Christoph Martin, Mannheim, all of Fed. Rep. of Germany

[73] Assignee: BASF Aktiengesellshaft, Ludwigshafen, Fed. Rep. of Germany

[21] Appl. No.: 724,056

[22] Filed: Jul. 1, 1991

[30] Foreign Application Priority Data

Jul. 4, 1990 [DE] Fed. Rep. of Germany ........ 4021274

[51] Int. Cl.$^5$ .................. C12P 25/00; C12N 1/16; C07D 475/14
[52] U.S. Cl. ........................... 435/66; 435/85; 435/86; 544/251
[58] Field of Search .............. 435/85, 86, 66, ; 544/251; 514/251

[56] References Cited

U.S. PATENT DOCUMENTS

| | | | |
|---|---|---|---|
| 2,324,800 | 7/1943 | Pasternack et al. | 544/251 |
| 2,464,243 | 3/1949 | Legg et al. | 544/251 |
| 2,571,896 | 10/1951 | Keresztesy et al. | 544/251 |
| 2,603,633 | 7/1952 | Dale | 544/251 |
| 2,797,215 | 6/1957 | Dale | 544/251 |
| 2,822,361 | 2/1958 | Morehouse | 544/251 |
| 4,165,250 | 8/1979 | Epstein et al. | 435/267 |
| 4,567,262 | 3/1987 | Grimmer et al. | |
| 4,687,847 | 8/1987 | Grimmer et al. | 544/251 |
| 4,794,081 | 12/1988 | Kawai et al. | 435/85 |

FOREIGN PATENT DOCUMENTS

| | | | |
|---|---|---|---|
| 468524 | 10/1950 | Canada | 544/251 |
| 0211289 | 2/1987 | European Pat. Off. . | |
| 0231605 | 8/1987 | European Pat. Off. . | |
| 112538 | 4/1990 | European Pat. Off. . | |
| 2920592 | 12/1980 | Fed. Rep. of Germany . | |
| 3420310 | 4/1985 | Fed. Rep. of Germany . | |
| 9101320 | 2/1991 | World Int. Prop. O. | 544/251 |

*Primary Examiner*—Herbert J. Lilling
*Attorney, Agent, or Firm*—Keil & Weikauf

[57] ABSTRACT

A method of purifying ferment-produced riboflavin, wherein the impure riboflavin is suspended in water or dilute aqueous acid, and the suspension is heated at a temperature of from 75° to 130° C. for from 0.3 to 3 hours with stirring, during which time crystal transformation takes place, after which the mixture is cooled and the purified product is isolated in known manner.

6 Claims, No Drawings

METHOD OF PURIFYING FERMENT-PRODUCED RIBOFLAVIN

The present relates to a method of purifying riboflavin (vitamin $B_2$) which has been prepared by microbiological action, by heating the impure riboflavin in the presence of water or aqueous acid.

The preparation of riboflavin by microbial fermentation processes is known. For example, riboflavin can be prepared by fermentation of *Ashbya gossypii* or *Eremothecium ashbyii* (DE 2,920,592), by fermentation of yeast of type Saccharomyces or a variant thereof (EP-A 211,289) or by way of *Candida flareri* (EP-A 231,605) or by way of *Bacillus subtilis* (DE-A 3,420,310). Riboflavin made in this way on an industrial scale is generally used as a feed supplement. In such processes, the end product can be obtained as a riboflavin concentrate simply by concentrating the culture fluid produced, together with the remaining biomass, by evaporation. This gives a product which contains from 20 to 40% w/w of riboflavin depending on the productivity of the strain producing the riboflavin.

A product having a riboflavin content of from about 40 to 60% w/w is obtained, for example, by decanting the culture fluid once or a number of times in a special manner (cf. DE-A 2,920,591).

Thus ferment-produced riboflavin is sold commercially as a feed supplement in various grades. The feed-grade market products generally have riboflavin contents of from 50 to about 96% w/w. In particular, products are sold which have contents of approx. 65%, approx. 80%, and approx. 96%, by weight, of riboflavin.

However, such products do not comply with pharmacological stipulations for riboflavin. For example, the pharmacopoeias specify a minimum riboflavin content of 98% w/w.

According to the process described in EP 137,226, relatively pure riboflavin can be obtained by producing riboflavin in a special culture and heating an aqueous solution thereof, from which the solids are separated and from which the riboflavin is then isolated by crystallization. The drawback of this procedure is that extremely large quantities of water are required to form a solution of the riboflavin, which is only sparingly soluble in water. For this reason, the process is not suitable for use on an industrial scale.

It is thus an object of the present invention to provide a method of purifying riboflavin which has been prepared by microbial fermentation, by means of which method such ferment-produced riboflavin can be obtained in a grade making it suitable for addition to foodstuffs and to pharmaceutical preparations. It is another, general, object of the invention to provide a simple method of substantially raising the riboflavin content of ferment-produced riboflavin.

The invention relates, therefore, to a method of purifying ferment-produced riboflavin, wherein the impure riboflavin is suspended in water or dilute aqueous acid, and the suspension is heated at a temperature of from 75° to 130° C. and preferably from 80° to 120° C. for from 0.3 to 3 hours and preferably from 1 to 2.5 hours, with stirring, after which the reaction mixture is cooled and the crystals thus formed are isolated by known methods.

Such heating in water or dilute aqueous acid presumably causes a change in crystal structure, as is evident from the fact that the mass of crystals becomes thick and pasty. Stirring is thus essential. Further heating causes a normal suspension to reform from which the riboflavin, now purified by crystal transformation can be isolated in conventional manner.

The amount of water used for this process is generally from about 10 to 30, preferably from 15 to 20, times the weight of the riboflavin.

The heating method proposed in the present invention makes it possible to improve the purity of riboflavin from about 96% to about 99%, from about 90% to about 97% and from about 65% to about 80%, by weight.

The purifying effect can be intensified by adding to the water from about 0.05 to 10% and preferably from 0.5 to 3% w/w of a water-soluble acid, preferably a mineral acid such as $H_2SO_4$, $H_3PO_4$ or HCl.

By appropriately heating the impure vitamin $B_2$ in dilute aqueous acid it is possible, for example, to increase the riboflavin content from about 96% to 100%, from about 90% to about 97% and from about 65% to about 90%, by weight.

By dilute aqueous acid we mean, for the purposes of the invention, a solution of a water-soluble acid, preferably a mineral acid which has no adverse effect on the riboflavin molecule. Examples of suitable water-soluble acids are organic acids such as formic acid, tartaric acid, citric acid and acetic acid, and mineral acids such as sulfuric acid, hydrochloric acid and phosphoric acid.

The type of acid used is not critical, provided it is completely soluble in water, does not attack the riboflavin molecule and its concentration is not high enough to cause dissolution of the riboflavin.

It is particularly advantageous to use such commercially available mineral acids as $H_2SO_4$, $H_3PO_4$ and HCl.

In the case of dilute sulfuric acid, it is particularly advantageous to use a solution having a molarity of from 0.1 to 1, and in the case of dilute phosphoric acid or dilute hydrochloric acid, one having a molarity of from 0.1 to 1.5.

The method of the invention makes it possible to purify ferment-produced riboflavin in an industrially simple manner.

The invention is illustrated below with reference to the following Examples. The contents of riboflavin given in the Examples were all determined as specified in the pharmacopoeia "Europe II".

EXAMPLE 1

100 g of a commercial riboflavin having a purity of 95.7% w/w were stirred into 2,000 ml of distilled water. The readily stirrable suspension was heated in a water-bath to 80° C. and crystal transformation occurred during the next 30 minutes. The viscous, pasty mass of crystals formed was further heated to 100° C. and again became a readily stirrable suspension. This was kept at 100° C. for about one hour and was then cooled to 30° C. and filtered. The filter cake was washed with 1,000 ml of warm water (40° C.) and then with 1,000 ml of methanol. After drying under reduced pressure at 80° C. the yield was 95.32 g of riboflavin having a purity of 98.9%.

EXAMPLE 2

25 g of a commercial riboflavin having a purity of 95.7% w/w were added to a mixture of 490 ml of demineralized water and 10 ml of concentrated $H_2SO_4$.

The resulting suspension was brought to the boil and thoroughly stirred for 1 hour at 95°-97° C. It was then cooled to 40° C. and the mother liquor was filtered off. The filter cake was washed with 500 ml of warm water (40° C.) and then with 500 ml of methanol. After drying under reduced pressure at 80° C., the yield was 23.49 g of riboflavin having a purity of 99.95%.

EXAMPLE 3

6,000 ml of demineralized water and 50 g of 85% phosphoric acid were placed in a stirred pressure vessel and 1,532 g of moist vitamin $B_2$ (dry substance 23% —equivalent to 352.36 g of dry vitamin $B_2$ having a purity of 90%) were added.

The vessel was sealed, and the mixture contained therein was heated to 120° C. and stirred at this temperature for 1 hour. The autogenous pressure was 1.1–1.3 bar. The mixture was then cooled to 40° C. The solids were then separated from the mother liquor by filtration under reduced pressure and the filter cake was washed with 3,000 ml of demineralized water and then with 2,000 ml of methanol. It was then dried under reduced pressure at 80° C. to give 318 g of vitamin $B_2$ having a purity of 96.8%.

EXAMPLE 4

Example 3 was repeated except that no phosphoric acid was added.

There were obtained 320 g of vitamin $B_2$ having a purity of 95.62%.

EXAMPLE 5

8,000 ml of demineralized water were placed in a stirred pressure vessel, and 400 g of a commercial feed-grade vitamin $B_2$ product containing 65% of vitamin $B_2$ were added with stirring. The vessel was sealed, and the suspension contained therein was heated to 120° C. and stirred at this temperature for 1 hour. It was then cooled to 40° C. The solids were then separated from the mother liquor by filtration under reduced pressure and the filter cake was washed with 4,000 ml of water followed by about 2,000 ml of methanol. After drying under reduced pressure at 80°-90° C., the yield was 315 g of vitamin $B_2$ having a purity of 79.4%.

EXAMPLE 6

Using the apparatus described in Example 5, there were added to a mixture of 8,000 ml of demineralized water and 60 ml of 85% phosphoric acid 400 g of a commercial vitamin $B_2$ product containing 65% of vitamin $B_2$, and the resulting suspension was stirred at 120° C. for 1 hour. The mixture was worked up as described in Example 5 to give 293.8 g of vitamin $B_2$ having a purity of 90.5%.

We claim:

1. A method of purifying ferment-produced riboflavin, wherein the impure riboflavin obtained after fermentation is suspended in water or dilute aqueous acid in an amount of 10 to 30 times the weight of the riboflavin without dissolving the riboflavin, and the resulting suspension is heated at a temperature of from 75° to 130° C. for from 0.3 to 3 hours with stirring while maintaining the suspension, and the crystals formed on cooling are isolated.

2. A method as defined in claim 1, wherein the impure riboflavin is suspended in water and the suspension is heated at from 80° to 120° C. while maintaining the suspension.

3. A method as defined in claim 1, wherein the impure riboflavin is suspended in dilute aqueous mineral acid and the suspension is heated at from 80° to 120° C.

4. A method as defined in claim 1, wherein the dilute aqueous acid used is sulfuric acid having a molarity of from 0.1 to 1.

5. A method as defined in claim 1, wherein the dilute aqueous acid used is phosphoric or hydrochloric acid having a molarity of from 0.1 to 1.5.

6. A method as defined in claim 1, wherein the suspension is heated at from 80° C. to 120° C. for from 1 to 2.5 hours.

* * * * *